United States Patent
Hayakawa (10) Patent No.: US 11,857,690 B2
(45) Date of Patent: Jan. 2, 2024

(54) METHOD FOR STERILIZING INTERIOR OF ASEPTIC FILLER CHAMBER

(71) Applicant: Dai Nippon Printing Co., Ltd., Tokyo (JP)

(72) Inventor: Atsushi Hayakawa, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 288 days.

(21) Appl. No.: 17/309,383

(22) PCT Filed: Dec. 9, 2019

(86) PCT No.: PCT/JP2019/048082
§ 371 (c)(1),
(2) Date: May 24, 2021

(87) PCT Pub. No.: WO2020/122015
PCT Pub. Date: Jun. 18, 2020

(65) Prior Publication Data
US 2022/0031891 A1    Feb. 3, 2022

(30) Foreign Application Priority Data

Dec. 12, 2018 (JP) ................. 2018-232801

(51) Int. Cl.
*A61L 2/20* (2006.01)
*A61L 2/06* (2006.01)
*A61L 2/18* (2006.01)

(52) U.S. Cl.
CPC ............. *A61L 2/208* (2013.01); *A61L 2/06* (2013.01); *A61L 2/18* (2013.01); *A61L 2202/15* (2013.01); *A61L 2202/23* (2013.01)

(58) Field of Classification Search
CPC ... A61L 2/06; A61L 2/18; A61L 2/186; A61L 2/208; A61L 2202/15; A61L 2202/23;
(Continued)

(56) References Cited

U.S. PATENT DOCUMENTS 9,050,381 B2   6/2015  Iwashita et al.
2014/0196415 A1*  7/2014  Drenguis ............... B67C 3/001
                                                  53/493
(Continued)

FOREIGN PATENT DOCUMENTS

CN    204842373 U    12/2015
CN    107922177 A     4/2018
(Continued)

OTHER PUBLICATIONS

International Search Report and Written Opinion (Application No. PCT/JP2019/048082) dated Feb. 18, 2020.

*Primary Examiner* — Jennifer Wecker
*Assistant Examiner* — Brady C Pilsbury
(74) *Attorney, Agent, or Firm* — BURR PATENT LAW, PLLC (57) ABSTRACT

In the COP treatment and the SOP treatment of the interior of a chamber of an aseptic filler, any cleaning liquid or aseptic water remaining in the chamber is quickly removed before spray of a sterilizer containing peracetic acid or hydrogen peroxide.
A transfer device for transferring a container in the chamber of the aseptic filler is driven to remove the cleaning liquid sued for the COP treatment or the aseptic water used for the SOP treatment.

15 Claims, 5 Drawing Sheets

(58) Field of Classification Search
CPC ... B67C 3/005; B67C 2003/228; B65B 55/06; B65B 55/10; B65B 2210/06; B65B 2210/08
See application file for complete search history.

(56) References Cited

U.S. PATENT DOCUMENTS

| | | |
|---|---|---|
| 2018/0208446 A1 | 7/2018 | Hayakawa et al. |
| 2020/0165115 A1 | 5/2020 | Hayakawa |

FOREIGN PATENT DOCUMENTS

| | | |
|---|---|---|
| JP | H05-051088 A | 3/1993 |
| JP | H11-208782 A1 | 8/1999 |
| JP | 2000-062734 A | 2/2000 |
| JP | 2010-189034 A1 | 9/2010 |
| JP | 2011-147673 A1 | 8/2011 |
| JP | 2014-055026 A1 | 3/2014 |
| JP | 2017-154822 A1 | 9/2017 |
| JP | 2018-188206 A | 11/2018 |

* cited by examiner

METHOD FOR STERILIZING INTERIOR OF ASEPTIC FILLER CHAMBER

TECHNICAL FIELD

The present invention relates to a method for sterilizing the interior of a chamber of an aseptic filler before filling a container, such as a plastic bottle, a paper container, a cup, a tray or a pouch, with a food, a drink or the like.

BACKGROUND ART

With an aseptic filler that aseptically fills a container, such as a plastic bottle, a paper container, a cup, a tray or a pouch, with a tea drink, mineral water, a juice, a soup, an energy drink, milk, a milk beverage, a sauce, a broth or the like, when changing the filling content, the interior of the content supply piping is first subjected to a CIP (Cleaning in Place) treatment and then to a SIP (Sterilizing in Place) treatment.

The CIP treatment is performed by flowing a cleaning liquid containing water and an alkaline chemical agent as an additive, such as caustic soda, through a flow path from the interior of a pipe line of a content filling path to a filling nozzle of the filler, and thereafter flowing a cleaning liquid containing water and an acidic chemical agent as an additive. As a result of this, any remainder of the previously used content or the like adhering to the inside of the content filling path is removed.

The SIP treatment is performed by, for example, flowing steam, hot water or the like through the flow path which has been cleaned by the above-described CIP treatment. As a result of this, the interior of the content filling path is sterilized and brought into an aseptic state.

The aseptic filler includes a sterilizing portion that sterilizes a container to be filled with a content, a rinsing portion that rinses the sterilized container, a filling portion that fills the sterilized container with a content sterilized by a content sterilization apparatus, and a sealing portion that seals the container filled with the content in an aseptic atmosphere, for example. These portions are arranged in chambers that shield the portions from the outside, and an aseptic atmosphere has to be maintained in each chamber during operation of the aseptic filler.

Droplets or the like of the content used in the previous filling operation may be deposited on the inside of the filling portion chamber or the sealing portion chamber. When changing the kind of the filling content, the interior of the chamber is subjected to a COP (Cleaning out of Place) treatment in order to remove any droplets or the like of the content deposited on the inner wall of the chamber and the outer surface of the equipment, such as the filler, in the chamber in the previous filling operation. The COP treatment is performed by spraying a shower of water or the like into the aseptic chamber, for example.

Further, since there is also a risk that bacteria enter the aseptic chamber during various operations when changing the kind of the content, an SOP (Sterilizing out of Place) treatment is also performed on the interior of the aseptic chamber. In a conventional method of performing the SOP treatment on the interior of a chamber, spaying of peracetic acid into the chamber, spraying of aseptic water into the chamber, blowing of heated air into the chamber, spraying of hydrogen peroxide into the chamber, and blowing of heated air into the chamber are sequentially performed (see Patent Literature 1).

Patent literature 2 proposes a sterilization of the interior of a chamber that includes a step of spraying hot water, a step of spraying heated peracetic acid-based sterilizer, and a step of rinsing by spraying heated aseptic water (see Patent Literature 2). Further, there is a method of sterilizing the interior of a chamber that involves spraying a low-concentration sterilizer and then drying the sterilizer (see Patent Literature 3).

Patent Literature 4 proposes that after a COP treatment is performed by spraying an alkaline cleaner into a chamber and then spraying aseptic water, a SOP treatment is performed by sequentially performing spraying of peracetic acid, spraying of aseptic water, spraying of hydrogen peroxide, blowing of hot air, and blowing of cold air (see Patent Literature 4).

CITATION LIST

Patent Literature

Patent Literature 1: Japanese Patent Laid-Open No. 11-208782
Patent Literature 2: Japanese Patent Laid-Open No. 2010-189034
Patent Literature 3: Japanese Patent Laid-Open No. 2011-147673
Patent Literature 4: Japanese Patent Laid-Open No. 2014-55026

SUMMARY OF INVENTION

Technical Problem

In an aseptic filler that fills a sterilized container with a sterilized content in an aseptic atmosphere and seals the container, the SOP treatment is performed in order to ensure the aseptic atmosphere in the chamber of the aseptic filler before starting production.

In the SOP treatment, peracetic acid or hydrogen peroxide is used as a sterilizer. In Patent Literatures 2 and 3, such SOP treatment methods are described. On the other hand, Patent Literatures 1 and 4 propose two-stage SOP treatments in which after a sterilization with peracetic acid is performed, a sterilization with hydrogen peroxide is performed. The sterilizer containing peracetic acid is liquid so that parts that become wet with liquid are sterilized, and the sterilization with hydrogen peroxide is advantageous for a clearance of a packing or the like into which liquid cannot penetrate. After a hydrogen peroxide solution is sprayed into the chamber, heated aseptic air is blown into the chamber. In this process, the hydrogen peroxide solution having been sprayed into the chamber is heated, vaporized and discharged. The hydrogen peroxide in the hydrogen peroxide solution is heated and vaporized, and the vaporized hydrogen peroxide can enter any clearance into which the sterilizer containing peracetic acid has been unable to penetrate, and sterilize the part that has not been sterilized by the sterilizer containing peracetic acid.

Typically, the sterilizer containing peracetic acid is sprayed into the chamber, aseptic water is then sprayed into the chamber to wash away the sprayed sterilizer containing peracetic acid, and the hydrogen peroxide solution is then sprayed into the chamber. In this process, if the hydrogen peroxide solution is sprayed into the chamber while the aseptic water remains in the chamber, the hydrogen peroxide solution is mixed with the aseptic water remaining in the chamber, and the concentration of hydrogen peroxide in the liquid mixture is lower than the concentration of hydrogen peroxide in the hydrogen peroxide solution sprayed into the chamber. As a result, the sterilizing effect of the spraying of the hydrogen peroxide solution tends to decrease. To avoid this, the spray of the hydrogen peroxide solution into the chamber is not performed until the aseptic water remaining in the chamber is removed by air-drying or being dried by aseptic air blown into the chamber. The spray of the hydrogen peroxide solution into the chamber is performed after it is visually checked that any aseptic water in the chamber is removed by air-drying or being dried by aseptic air.

When the interior of the chamber is sterilized with a sterilizer containing peracetic acid after the COP treatment in which the interior of the chamber is cleaned with a cleaning liquid and the cleaning liquid is washed away with water, again, the sterilizing effect of the sterilizer containing peracetic acid sprayed into the chamber decreases if the concentration of peracetic acid in the sterilizer containing peracetic acid decrease because of the water remaining in the chamber.

If the sterilizer containing peracetic acid and the hydrogen peroxide solution are sprayed into the chamber after waiting until the previously sprayed aseptic water is removed, the time required for the SOP treatment is extended, and the productivity of the aseptic filler decreases. It is required to quickly remove the water before spraying the sterilizer containing peracetic acid and the hydrogen peroxide solution when performing the SOP treatment on the interior of the aseptic filler. An object of the present invention is to solve the problem described above, and provide a method for sterilizing the interior of a chamber of an aseptic filler that improves the productivity of the aseptic filler by reducing the time required for the SOP treatment by quickly removing any remaining water when performing the SOP treatment on the interior of the chamber of the aseptic filler.

Solution to Problem

A method for sterilizing an interior of an aseptic filler chamber according to the present invention is a method for sterilizing an interior of a chamber of an aseptic filler before operation of the aseptic filler, the aseptic filler filling a sterilized container with a sterilized content in an aseptic atmosphere and sealing the container filled with the content, wherein after the interior of the chamber of the aseptic filler is cleaned by spraying a cleaning liquid into the chamber, a transfer device for transferring the container is driven to remove any of the cleaning liquid deposited on the transfer device, and a sterilizer is then sprayed into the chamber of the aseptic filler.

In the method for sterilizing an interior of an aseptic filler chamber according to the present invention, the sterilizer contains hydrogen peroxide.

In the method for sterilizing an interior of an aseptic filler chamber according to the present invention, the sterilizer contains peracetic acid.

In the method for sterilizing an interior of an aseptic filler chamber according to the present invention, the cleaning liquid is aseptic water.

In the method for sterilizing an interior of an aseptic filler chamber according to the present invention, when driving the transfer device, heated aseptic air is blown into the chamber of the aseptic filler.

In the method for sterilizing an interior of an aseptic filler chamber according to the present invention, transfer devices in a plurality of chambers of the aseptic filler are driven on a chamber basis.

Advantageous Effects of Invention

According to the present invention, when performing the COP treatment or the SOP treatment on the interior of a chamber of an aseptic filler, after a cleaning liquid is sprayed into the chamber of the aseptic filler, a transfer device for transferring a container is driven to remove any cleaning liquid deposited on the transfer device, so that any cleaning liquid remaining in the chamber of the aseptic filler can be quickly removed. After that, a sterilizer containing hydrogen peroxide or a sterilizer containing peracetic acid is sprayed into the chamber of the aseptic filler. Therefore, the concentration of hydrogen peroxide or peracetic acid in the sprayed sterilizer does not decrease, so that the interior of the chamber of the aseptic filler can be sterilized with reliability. Further, since the time required for the SOP treatment is reduced, the productivity of the aseptic filler can be improved.

DESCRIPTION OF EMBODIMENTS

In general, an aseptic filler includes a sterilizing portion that receives a container supplied to the aseptic filler and sterilizes the supplied container, a filling portion that fills the sterilized container with a sterilized content in an aseptic atmosphere, and a sealing portion that seals the container filled with the content in an aseptic atmosphere. However, the configuration of the aseptic filler varies depending on the container that is to be aseptically filled.

For example, when the container is a bottle, the aseptic filler includes a heating portion that receives a preform supplied to the aseptic filler and heats the preform to a molding temperature, a molding portion that molds the heated preform into a container, an inspecting portion that inspects the molded bottle, a bottle sterilizing portion that sterilizes the inspected bottle, an air rinsing portion that air-rinses the sterilized bottle, a filling portion that fills the sterilized bottle with a content sterilized by a content sterilization apparatus in an aseptic atmosphere, a sealing portion that seals the bottle filled with the content with a lid material in an aseptic atmosphere, and a discharging portion that discharges the sealed bottle. The aseptic filler for a bottle may not include the inspecting portion and the air rinsing portion. There is an aseptic filler that has a preform sterilizing portion that sterilizes the supplied preform before heating. The aseptic filler having the preform sterilizing portion may not include the bottle sterilizing portion.

When the container is a paper container, the aseptic filler includes a bottom part forming portion that receives a sleeve supplied to the aseptic filler, sterilizes surfaces to be the outer surface of the paper container, and forms a bottom part, a sterilizing portion that sterilizes the inner surface of the paper container with the bottom part formed, a filling portion that fills the paper container with the inner surface sterilized with a sterilized content, and a sealing portion that seals the paper container filled with the content. Aseptic fillers for different containers have different configurations.

Each portion of the aseptic filler is shielded in a chamber. With the aseptic filler for a bottle, the heating portion and the molding portion may be shielded in a single chamber. The sealing portion and the discharging portion may also be shielded in a single chamber. Further, the filling portion, the sealing portion and the discharging portion may also be shielded in a single chamber.

With the aseptic filler for a paper container, the bottom part forming portion, the sterilizing portion, the filling portion and the sealing portion are shielded in a single chamber. However, the bottom part forming portion, the sterilizing portion, the filling portion and the sealing portion may be each shielded in a different chamber. The configuration of each portion varies depending on the container to be handled by the aseptic filler, and the chamber shielding each portion also varies depending on the container to be handed by the aseptic filler.

During operation of the aseptic filler for a bottle, aseptic air sterilized by an aseptic filter is supplied to the chamber for the bottle sterilizing portion, the chamber for the air rinsing portion, the chamber for the filling portion, the chamber for the sealing portion and the chamber for the discharging portion, and the aseptic condition of the aseptic filler is maintained by establishing a positive pressure in each chamber. The positive pressure established is the highest in the chamber for the filling portion and decreases as it goes upstream, specifically, is set to be lower in the chamber for the air rinsing portion and even lower in the chamber for the bottle sterilizing portion. For example, provided that the pressure in the chamber for the filling portion is 20 Pa to 40 Pa, the pressures in the other chambers are lower than the pressure in the chamber for the filling portion. With the aseptic filler having a preform sterilizing portion, the heating portion and the molding portion are also each covered by a chamber, and aseptic air is supplied into the chamber for the heating portion and the chamber for the molding portion to maintain a positive pressure in the chambers.

Figure 1:
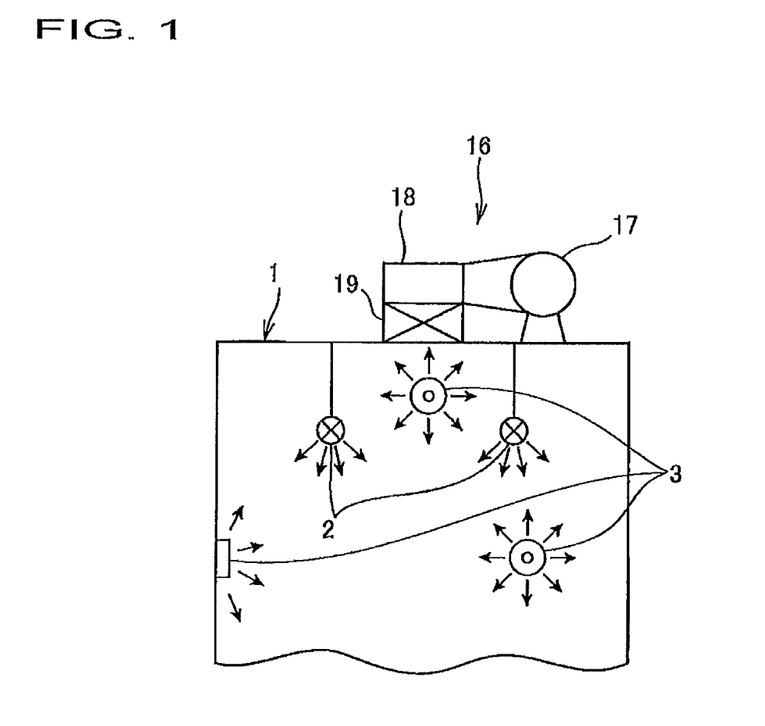
FIG. 1 is a schematic diagram showing an arrangement of nozzles in a chamber of an aseptic filler according to an embodiment of the present invention.

The interiors of the chamber for the bottle sterilizing portion, the chamber for the air rinsing portion, the chamber for the filling portion, the chamber for the sealing portion and the chamber for the discharging portion are subjected to a COP treatment and a SOP treatment before operation of the aseptic filler. To this end, as shown in FIG. 1, in a chamber 1 for the aseptic filler, a rotary nozzle 2 that sprays a cleaning liquid and a sterilizer containing peracetic acid, and a twin-fluid nozzle 3 that sprays a sterilizer containing hydrogen peroxide are provided. The rotary nozzle 2 is a nozzle that sprays a liquid supplied thereto into the chamber 1 while being rotated by the pressure of the liquid being supplied. The twin-fluid nozzle 3 is supplied with a sterilizer containing hydrogen peroxide and compressed air, and sprays the sterilizer containing hydrogen peroxide into the chamber 1 under the pressure of the compressed air. The nozzles provided in the chamber 1 are not limited to the rotary nozzle 2 and the twin-fluid nozzle 3, but can be any nozzle having a different structure that can spray a cleaner, an aseptic water and a sterilizer containing hydrogen peroxide into the chamber 1.

With the aseptic filler for a bottle, a sterilizer is sprayed into the chamber for the bottle sterilizing portion during operation of the aseptic filler, and therefore, the interior of the chamber for the bottle sterilizing portion need not be subjected to the SOP treatment. With the aseptic filler having the preform sterilizing portion, the interior of the chamber covering the heating portion and the molding portion is subjected to the SOP treatment.

With an aseptic filler intended for a container other than a bottle, the sterilizing portion, the filling portion and the sealing portion may be shielded in a single chamber. In such a case, the interior of the single chamber is subjected to the COP treatment and the SOP treatment.

Before the SOP treatment of the interior of each chamber, the chamber for the filling portion that performs filling with the content and the chambers downstream thereof are subjected to the COP treatment. The interior of any chamber that is badly contaminated with the content scattered in the chamber is cleaned by spraying warm water, hot water, or a cleaning liquid such as an alkaline cleaning liquid or an acidic cleaning liquid, into the chamber. The contamination of the chambers for the molding portion and the bottle sterilizing portion is limited, so that these chambers need not be subjected to the COP treatment.

When changing the content after a continuous operation of the aseptic filler filling containers with a content, or if the interior of a chamber is contaminated with droplets of the content after a continuous operation for a long time, the operation of the aseptic filler is stopped, and the chambers of the aseptic filler are subjected to the COP treatment and the SOP treatment. The interior of any chamber that is not contaminated with the content is subjected to only the SOP treatment.

For the COP treatment for cleaning the interior of the chamber 1 contaminated with the content, an alkaline cleaning liquid is first sprayed into the chamber 1. The alkaline cleaning liquid contains an inorganic basic compound such as sodium hydroxide or potassium hydroxide, or an organic basic compound such as ethanolamine or diethylamine, and may further contain a metal-ion blocking agent such as an alkali metal salt, an alkaline earth metal salt or an ammonium salt of an organic acid, or an ethylenediamine tetraacetic acid, an anionic surfactant, a cationic surfactant, a nonionic surfactant such as a polyoxyethylene alkylphenyl ether, a solubilizer such as sodium cumenesulfonate, a metal salt of an acid-based polymer such as polyacrylic acid, a corrosion inhibitor, a preservative, an antioxidant, a dispersant, a defoaming agent or the like.

After the alkaline cleaning liquid is sprayed, an acidic cleaning liquid may be sprayed. The acidic cleaning liquid is an inorganic acid such as hydrochloric acid, nitric acid or phosphoric acid, or an organic acid such as acetic acid, formic acid, octanoic acid, oxalic acid, citric acid, succinic acid or gluconic acid, and may contain an anionic surfactant, a cationic surfactant, a nonionic surfactant such as a polyoxyethylene alkylphenyl ether, a solubilizer such as sodium cumenesulfonate, an acid-based polymer such as polyacrylic acid, a corrosion inhibitor, a preservative, an antioxidant, a dispersant, a defoaming agents or the like. When the contamination with the content remains after the spray of the alkaline cleaning liquid, the spray of the acidic cleaning liquid is performed. Alternatively, the spray of the alkaline cleaning liquid may be omitted, and only the spray of the acidic cleaning liquid may be performed. The spray of the alkaline cleaning liquid and the spray of the acidic cleaning liquid may be alternately performed.

The cleaning may be performed using water at room temperature, warm water or hot water, without using the alkaline cleaning liquid and the acidic cleaning liquid. Alternatively, after the cleaning with the alkaline cleaning liquid and the acidic cleaning liquid, the cleaning with water at room temperature, warm water or hot water may be performed, which also serves to wash the alkaline cleaning liquid and the acidic cleaning liquid away. These cleaning liquids can be used in any combination in any order. Here, the warm water herein is water at a temperature equal to or higher than 40° C. and lower than 100° C., and the hot water herein is water at a temperature equal to or higher than 100° C. and equal to or lower than 130° C.

If the alkaline cleaning liquid is heated to 50° C. or higher, the alkaline cleaning liquid has a sterilizing effect. Therefore, by spraying the alkaline cleaning liquid heated to 50° C. or higher into the chamber 1, a sterilizing effect is also expected.

After the cleaning liquid is sprayed into the chamber 1, transfer devices that convey the containers are driven to remove any cleaning liquid deposited on the transfer devices. When the cleaning liquid is the alkaline cleaning liquid or acidic cleaning liquid for example, the alkaline cleaning liquid or acidic cleaning liquid may be washed away by additionally using room temperature water, warm water or hot water as a cleaning liquid. The water used may be aseptic water. In order to prevent the interior of the chamber from being contaminated with bacteria contained in the water sprayed thereto, aseptic water is preferably used. The aseptic water herein is water sterilized by being heated at 121.1° C. or higher for 4 minutes or longer or by being passed through an aseptic filter. If a sterilizer containing peracetic acid is used in the subsequent sterilizer spray, the water may be non-aseptic water. This is because the sterilizer containing peracetic acid sterilizes any water remaining in the chamber 1.

The temperature of the water sprayed into the chamber after the interior of the chamber is cleaned with the alkaline cleaning liquid or acidic cleaning liquid is 20° C. to 100° C., preferably 60° C. to 100° C. By setting the temperature of the water to 60° C. or higher, not only the improvement of the cleaning ability but also a sterilizing effect against heat-resistant fungi and heat-resistant yeast damaged by chemical agents such as alkali used in the COP treatment is expected.

Figure 2:
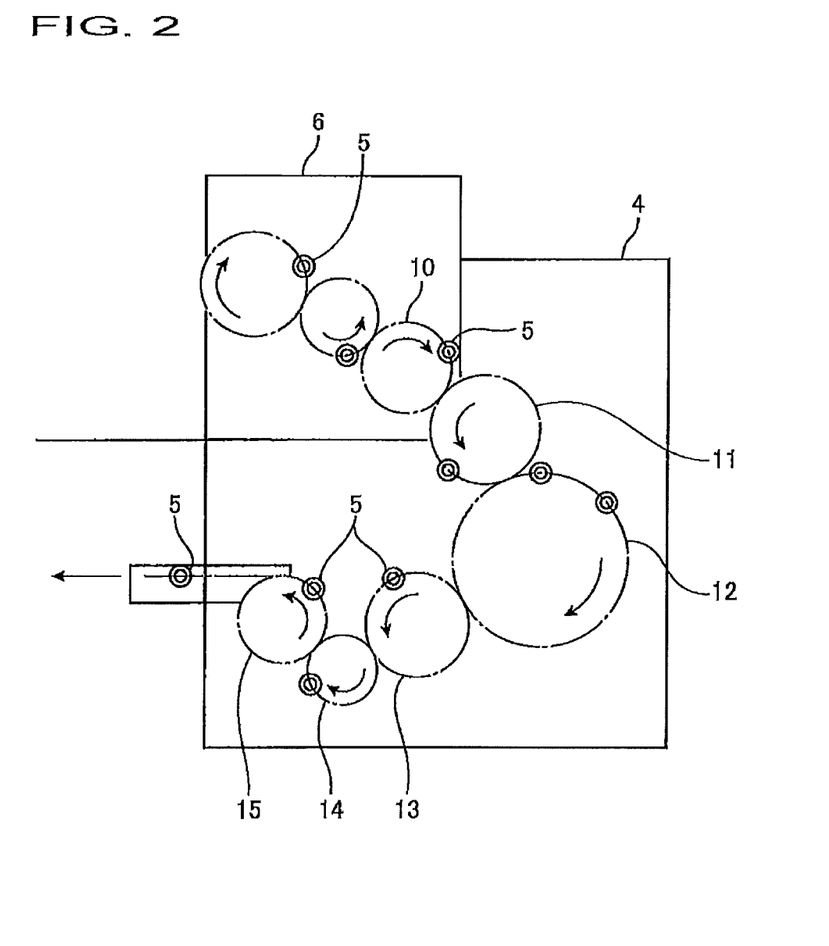
FIG. 2 is a schematic plan view of the interior of a filling portion chamber of an aseptic filler for bottles according to the embodiment of the present invention.

Driving of the transfer devices that convey bottles will be described with reference to FIG. 2. FIG. 2 is a schematic plane view of the interior of a filling portion chamber 4 of an aseptic filler for bottles according to an embodiment of the present invention. FIG. 2 shows a part of the aseptic filler a filling portion, a sealing portion and a discharging portion of which are shielded by a single filling portion chamber. A bottle, which is a sterilized container, is passed from a wheel 10 in an air rinsing portion chamber 6 that shields an air rinsing portion to the interior of the filling portion chamber 4. Viewed from the upstream side to the downstream side of the conveyance path of the bottle 5, an introduction wheel 11, a filling wheel 12, an intermediate wheel 13, a capper wheel 14 and a discharging wheel 15 are arranged in the listed order. These wheels 11 to 15 are driven to rotate at substantially the same circumferential velocity.

Grippers having a shape like a pair of scissors that hold and release a neck portion of the bottle 5 are arranged at predetermined intervals around each of the wheels 11 to 15. The grippers can rotate about the central axes of the respective wheels 11 to 15 along with the respective wheels 11 to 15.

Although the gripper is a well-known component and therefore will not be described in detail, the grippers are opened and closed at a position where the wheels are adjacent to each other by the action of a cam or the like, and the bottle 5 is thereby passed from the gripper on the upstream-side wheel to the gripper on the downstream-side wheel. In this way, the bottle 5 continuously travels from the introduction wheel 11 to the discharging wheel 15 via the filling wheel 12, the filling wheel 12 and the like.

A filling nozzle, which rotates along with the filling wheel 12, is connected to the filling wheel 12, which is attached, in a horizontal orientation, to a vertical shaft installed on a base, and grippers are provided around the filling wheel 12.

In addition, a plurality of pipe-shaped filling nozzles for filling bottles 5 with a drink or the like are arranged around the charging wheel 12 in association with the grippers. Each filling nozzle is arranged in a vertical orientation with the mouth at the lower end thereof facing the mouth portion of the bottle 5 gripped by the gripper. The filling nozzle may be fixed with respect to the filling wheel 12 or may be able to reciprocate in the vertical direction. If the filling nozzle can reciprocate in the vertical direction, the filling nozzle can be inserted into the bottle 5 to supply a drink or the like as a content into the bottle 5.

After the drink or the like is sterilized, the drink or the like is stored in a storage tank (not shown) and is supplied from the storage tank to the filling nozzles through a pipe line. In order to distribute the drink or the like supplied from the storage tank to the filling nozzles rotating, the vertical shaft is provided with an upper rotary joint and an upper manifold. The drink or the like from the storage tank enters a cavity in the vertical shaft and is discharged from the filling nozzles into the bottles 5 via the upper rotary joint and the upper manifold.

The filling nozzle is provided with a valve that allows a desired amount of the drink or the like to be supplied into the bottle 5. The aseptic filler includes a CIP treatment apparatus that performs the CIP treatment for cleaning the interior of the drink supply piping from the storage tank to the filling nozzles, and a SIP treatment apparatus that performs the SIP treatment for sterilization. For the CIP treatment and the SIP treatment, a cup-shaped closing device of the filling nozzle is provided to open and close the mouth at the lower end of the filling nozzle. The cup-shaped closing devices of the filling nozzles are arranged around the filling wheel 12 in association with the grippers and the filling nozzles.

The cup-shaped closing device of the filling nozzle can be moved by a cam device, an air cylinder device or the like in the radial direction of the filling wheel 12 and the vertical direction. The cup-shaped closing device of the filling nozzle is retracted inwardly in the radial direction when supplying the drink or the like from the charging nozzle into the bottle 5, and is moved outwardly in the radial direction to directly below the filling nozzle and then raised to block the mouth of the filling nozzle when closing the filling nozzle.

In addition to the cup-shaped closing devices of the filling nozzles, components of the CIP treatment apparatus include a lower manifold, a lower rotary joint, a cleaning liquid tank, and a pump. The lower rotary joint is attached to the vertical shaft. The lower manifold is fixed to the base. The cup-shaped closing device of the filling nozzle, the upper manifold, the lower manifold and the like are connected to each other by a pipe line. These components of the CIP treatment apparatus rotate along with the filling wheel 12.

Around the capper wheel 14 shown in FIG. 2, cappers are provided to cap the mouth portions of the bottles 5 filled with the drink or the like, although not shown. The capper rotates along the capper wheel 14 and screws a sterilized cap onto the mouth portion of the bottle 5.

The wheels 11 to 15 in the chamber cleaned with the cleaning liquid are rotated. After the spray of the cleaning liquid into the filling portion chamber 4, the wheels 11 to 15 transferring the bottles 5 are rotated, and any cleaning liquid deposited on devices rotating along with the wheels 11 to 15 is removed by the action of the centrifugal force produced by the rotation of the wheels 11 to 15.

The wheels 11 to 15 are rotated at a half or more of the rotating speed of the wheels during operation of the aseptic filler, preferably at the operating speed during manufacture. The wheels in the chambers are rotated at the same time at substantially the same number of revolutions. When each chamber is provided with a motor, and the rotation of the wheels can be controlled for each chamber, the wheels are rotated on a chamber basis. By rotating the wheels according to the stages of the COP treatment and the SOP treatment for each chamber, the COP treatment and the SOP treatment for each chamber can be quickly performed. By rotating the wheels, any aseptic water on devices and the wall in the chamber can be quickly removed. While the CIP treatment or SIP treatment of the interior of the drink supply piping is being performed, the clutch of the filling wheel 12 may be disengaged, and the other wheels than the filling wheel 12 may be rotated.

The sterilizer is then sprayed to the interior of the filling portion chamber 4 to sterilize devices and the wall in the filling portion chamber 4. When a sterilizer containing peracetic acid is sprayed, it is necessary to prevent a decrease of the sterilizing effect by preventing the concentration of peracetic acid in the sterilizer from decreasing because of the water remaining in the chamber. Before the sterilizer containing peracetic acid is sprayed, heated air is preferably blown into the filling portion chamber 4 to completely remove the remaining water. However, this takes a long time. By rotating the wheels 11 to 15, which are the transfer devices for the bottles 5, any cleaning liquid deposited on the wheels 11 to 15 and devices attached to the wheels 11 to 15 can be removed, and a decrease of the sterilizing effect of the sterilizer containing peracetic acid can be prevented.

When rotating the wheels 11 to 15, the wheels 11 to 15 may be intermittently rotated. By intermittently rotating the wheels, the cleaning liquid deposited on the wheels 11 to 15 and devices attached to the wheels 11 to 15 can be efficiently removed because of the accelerations that occur when the wheels start rotating and stop rotating. In addition, spindles of the cappers may be moved up and down, thereby removing water remaining on bellows protecting the spindles.

In the aseptic filler for bottles, the removal of the cleaning liquid by driving the transfer devices that convey containers is also performed in the chambers for other than the filling portion, the sealing portion and the discharging portion such as the heating portion, the molding portion, the sterilizing portion, the air rinsing portion and the like. The wheels are also rotated in the chambers other than the filling portion chamber 4. However, in the chamber for the heating portion, an endless chain for transferring preforms can be operated to remove aseptic water deposited on the endless chain and spindles thereof. In the chamber for the molding portion, wheels can be rotated to remove aseptic water deposited on the wheels, and dies, extension rods, valve blocks and the like thereof.

When removing the cleaning liquid by driving the transfer devices that convey containers, air is preferably blown into a chamber of the aseptic filler. By blowing heated aseptic air into a chamber, the removal of the cleaning liquid can be accelerated and completed in a shorter time. The air blown into the chamber is preferably heated. Further, the air blown into the chamber may be aseptic air. This is achieved by a heated aseptic air supply apparatus 16 provided on top of the chamber 1 shown in FIG. 1 supplying heated aseptic air into the chamber 1. The heated aseptic air is produced by a heating apparatus 18 heating air from a blower 17 and sterilizing the heated air through an aseptic filter 19. The heated aseptic air supply apparatus 16 includes the blower 17, the heating apparatus 18 and the aseptic filter 19.

After the cleaning liquid is removed in the chamber subjected to the COP treatment that involves spray of the cleaning liquid, the interior of the chamber is subjected to the SOP treatment. In the aseptic filler for bottles, the interiors of the chambers covering the heating portion and the molding portion of the aseptic filler having the preform sterilizing portion are not contaminated with the content, the COP treatment for the chambers may be omitted, and the interiors of the chambers may be subjected only to the SOP treatment. In the SOP treatment, a sterilizer containing peracetic acid is sprayed into the chamber, aseptic water is then sprayed to wash the sterilizer containing peracetic acid, a sterilizer hydrogen peroxide is then sprayed into the chamber, and the sterilizer containing hydrogen peroxide is then removed by being dried.

Alternatively, the sterilizer containing peracetic acid and the sterilizer containing hydrogen peroxide may be alternately sprayed. For example, the sterilizer containing peracetic acid is sprayed and then washed away with aseptic water, the aseptic water is then removed by driving the transfer devices that convey containers, and the sterilizer containing hydrogen peroxide is then sprayed and removed by being dried.

There is a SOP treatment that includes a step of spraying a sterilizer containing hydrogen peroxide, a step of removing the sterilizer containing hydrogen peroxide by drying the sterilizer, a step of spraying a sterilizer containing peracetic acid, and a step of washing the sterilizer containing peracetic acid away with aseptic water. The spray of the sterilizer containing peracetic acid and the spray of the sterilizer containing hydrogen peroxide may be alternately performed, or may be each performed multiple times.

When aseptic water is sprayed after the sterilizer containing peracetic acid is sprayed, and the sterilizer containing hydrogen peroxide is then sprayed, the transfer devices that convey containers is driven after the spray of the aseptic water to remove the aseptic water. The parts of the interior of the chamber that has come into contact with the sterilizer containing peracetic acid are perfectly sterilized by the sterilizer containing peracetic acid. However, there is a possibility that a small clearance into which the sterilizer cannot enter, a part the sprayed sterilizer cannot reach, or a part (such as a HEPA filter) that should not be actively sterilized with the sterilizer containing peracetic acid be not sterilized, or a peracetic acid-resistant bacterium (such as *Paenibacillus* or *Bacillus cereus*) be not killed. Therefore, in order to sterilize a small clearance into which the sterilizer containing peracetic acid cannot enter or a part that the sprayed sterilizer containing peracetic acid cannot reach, which can be left unsterilized by the sterilizer containing peracetic acid, with hydrogen peroxide gas produced from the sterilizer containing hydrogen peroxide, the spray of the sterilizer containing peracetic acid and the spray of the sterilizer containing hydrogen peroxide may be alternately performed.

The sterilizer containing peracetic acid herein is a sterilizer mainly composed of peracetic acid, and the concentration of peracetic acid is 500 ppm or higher, preferably from 1000 ppm to 5000 ppm. The sterilizer further contains at least hydrogen peroxide and acetic acid. If the sterilizer containing peracetic acid is heated to 40° C. to 95° C., preferably to 50° C. to 95° C., the sterilizing effect is improved.

After the sterilizer containing peracetic acid is sprayed into the chamber, aseptic water is sprayed into the chamber. By spraying aseptic water, the sterilizer containing peracetic acid is washed away from the interior of the chamber. The water used to wash the sterilizer containing peracetic acid away has to be aseptic water. This is intended to maintain the sterilized state by the sterilizer containing peracetic acid.

The transfer devices that convey containers in the chamber from which the sterilizer containing peracetic acid has been washed away with aseptic water is driven. With the aseptic filler for bottles, after the spray of the aseptic water into the chamber, the wheels 11 to 15 for transferring the bottles 5 are rotated, and any aseptic water deposited on the wheels 11 to 15 and devices rotating along with the wheels 11 to 15 is removed by the action of the centrifugal force produced by the rotation of the wheels 11 to 15.

After the aseptic water is removed, the sterilizer containing hydrogen peroxide is sprayed into the chamber of the aseptic filler. Before the spray of the sterilizer containing hydrogen peroxide into the chamber, the interior of the chamber is preferably dried as much as possible. If the interior is wet, there is a possibility that the hydrogen peroxide be dissolved in the remaining aseptic water so that the concentration of hydrogen peroxide in the sterilizer decreases, and the sterilizing effect be not exerted.

In order to efficiently remove the aseptic water remaining in each chamber in a short time, the wheels in each chamber are rotated. In this regard, the rotation speed of the wheels is preferably raised to the operating speed during production. The wheels may be intermittently rotated. While the wheels are rotating, aseptic air is preferably supplied to prevent bacteria from entering from the outside. Further, the aseptic air is preferably heated in order to accelerate the removal of the aseptic water. The aseptic air can be heated to 50° C. to 200° C. By rotating the wheels, aseptic water deposited on the wheels and devices rotating along with the wheels can be removed. In addition, the rotation of the wheels causes a flow of air around the wheels, and the flow of air collides with the wall surface of the chamber, thereby promoting the downward flow of the aseptic water on the wall surface and accelerating the removal of the aseptic water on the wall surface. If the pressure in the filling portion chamber 4 is raised to 30 Pa to 200 Pa by suppling the aseptic air, the aseptic water is efficiently removed. The aseptic water in the other chambers is efficiently removed by raising the pressure in the same manner.

As described above, heated aseptic air is preferably blown into the chamber while the wheels are rotating. However, if heated aseptic air is blown into the chamber after the wheels stop rotating, the removal of the aseptic water remaining in the chamber can be more quickly removed.

After the aseptic water in the chamber is removed, the sterilizer containing hydrogen peroxide is sprayed into the chamber. The sprayed sterilizer containing hydrogen peroxide appropriately contains 20 mass % to 65 mass of hydrogen peroxide. If the content is less than 20 mass %, the sterilizing power may be insufficient, and if the content is more than 65 mass %, handling becomes difficult for safety reasons. By spraying the sterilizer containing hydrogen peroxide, any part that has not been sterilized by the spray of the sterilizer containing peracetic acid is sterilized, and any bacteria that has not been killed by the sterilizer containing peracetic acid is killed.

After the spray of the sterilizer containing hydrogen peroxide into the chamber, heated aseptic air is blown into the chamber in order to gasify the hydrogen peroxide and sterilize the interior of the chamber. The temperature of the heated aseptic air can be 50° C. to 200° C. By blowing the heated aseptic air into the chamber, the hydrogen peroxide in the sterilizer containing hydrogen peroxide remaining in the chamber is gasified to sterilize any small clearance that the sterilizer containing peracetic acid has not been able to enter or any part that the sprayed sterilizer containing peracetic acid has not reached or kill any peracetic acid-resistant bacteria.

After it is checked that the sterilizer containing hydrogen peroxide in the chamber has been removed by blowing the heated aseptic air into the chamber, the interior of the chamber having been heated by the blowing of the heated aseptic air is ventilated and cooled by blowing aseptic air at room temperature into the chamber to remove any remaining hydrogen peroxide.

While the aseptic filler for bottles has been mainly described above, with the aseptic fillers for other containers than bottles, such as cups, trays, paper containers and pouches, the cleaning liquid or aseptic water can be removed in a shorter time and the productivity of the aseptic filler can be improved by driving the transfer devices that convey containers.

Figure 3:
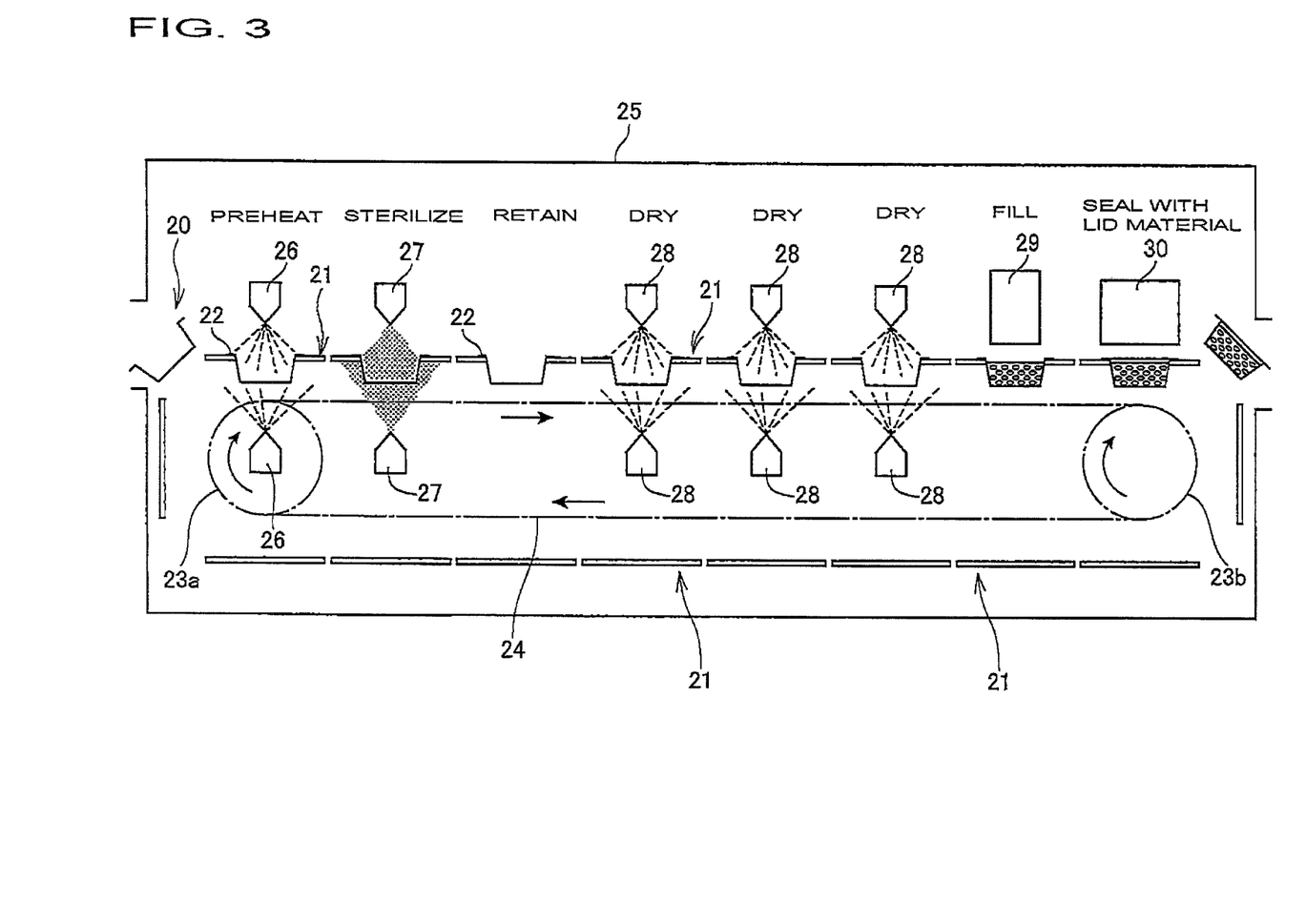
FIG. 3 is a schematic elevation view of an aseptic filler for trays according to an embodiment of the present invention.

FIG. 3 is a schematic elevation view of an aseptic filler for trays according to an embodiment of the present invention. Although the aseptic filler in FIG. 3 is shown as handling trays as containers, the aseptic filler having the same configuration can handle any cup-like container with a flange. A tray 20 supplied to the aseptic filler is held by a retainer 21. The retainer 21 has a flat plate portion, and a fitting opening, into which the tray 20 is fitted, is formed in the flat plate portion. The tray 20 is held with a container portion thereof being inserted in the fitting opening of the retainer 21 and a flange 22 thereof resting on the flat plate portion. A large number of retainers 21 are provided, and a succession of trays are conveyed with the flanges 22 being horizontally oriented. The retainers 21 are attached to the transfer devices continuously traveling. The transfer devices continuously traveling are attached to an endless chain 24 at predetermined distances, the endless chain 24 horizontally running between sprocket wheels 23a and 23b. Once the endless chain 24 is driven, the endless chain 24 holding the retainers 21 continuously runs, and thereby transferring the trays 20 in the aseptic filler.

As the trays 20 are conveyed in a chamber 25 of the aseptic filler shown in FIG. 3, the trays 20 are sterilized, filled with a content, and sealed. The chamber 25 houses a sterilizing portion, a filling portion and a sealing portion. The tray 20 supplied to the chamber 25 is held on the retainer 21 and preheated by hot air blasted from above and below by a preheating nozzle 26. The preheated tray 20 is sterilized with a sterilizer blasted from above and below by a sterilizer blasting nozzle 27. The tray 20 blasted with the sterilizer is retained for a predetermined time. After that, heated aseptic air is blasted from a dry air nozzle 28 to activate the sterilizer deposited on the surface of the tray 20 to sterilize the tray 20 and then remove the sterilizer by drying the sterilizer After that, the tray 20 is filled with a sterilized content by a filling apparatus 29, and the tray 20 filled with the content is thermally sealed with a sterilized lid material by a sealing apparatus 30. The sealed tray 20 is discharged from the chamber 25.

Before operation of the aseptic filler, the interior of the chamber 25 is subjected to the COP treatment and the SOP treatment. In this process, when removing the cleaning liquid used for the COP treatment or removing the aseptic water used for the SOP treatment, the transfer devices that convey the trays 20 are driven to remove the cleaning liquid and the aseptic water deposited on the transfer devices. That is, the endless chain 24 that conveys the retainers 21 yet to hold trays 20 is driven. By driving the endless chain 24, the cleaning liquid or aseptic water deposited on the endless chain 24 and the retainers 21 can be removed in a short time.

Figure 4:
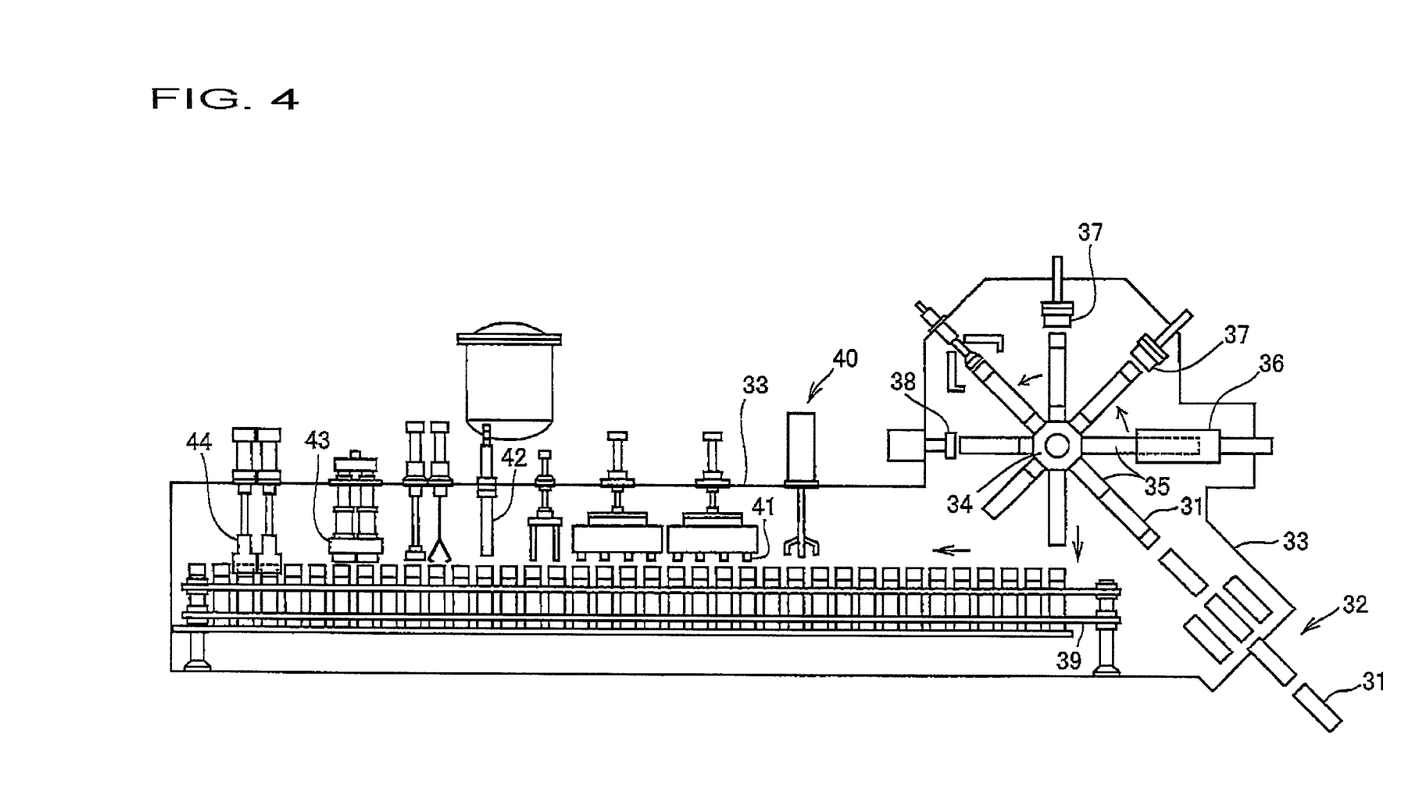
FIG. 4 is a schematic elevation view of an aseptic filler for paper containers according to an embodiment of the present invention.

FIG. 4 is a schematic elevation view of an aseptic filler for paper containers according to an embodiment of the present invention. A sleeve 31, which is a cylindrical body having a substantially rectangular cross section having a wall composed of at least a plurality of layers of paper, is introduced into a chamber 33 by a sleeve supply device 32. The sleeve 31 except for a part to be used to close the sleeve 31 is fitted onto a mandrel 35 provided on a turret 34. Further, a sterilization apparatus 36 sterilizes the inner surface of the part of the sleeve 31 that is to be closed and has not been fitted onto the mandrel 35 and the outer surface of the sleeve 31. After the sterilization, any remaining sterilizer is removed by hot air blasted by a drier device 37.

Further, the sleeve 31 is folded along a line that defines the bottom part of the paper container by a bottom part folding device, and the part having been heated by the drier device 37 is crimped by a bottom part sealing device 38. In this way, the sleeve 31 is closed at one of the open ends thereof and shaped into a paper container having the shape of a bottomed cylinder.

The formed paper containers are intermittently conveyed by a conveyor 39, and a nozzle blasts a sterilizer gas generated by a sterilizer gas generator 40 to the inner surfaces of the paper containers. The sterilizer blasted to the paper containers is removed by hot air blasted from hot air nozzles 41 to the inner surfaces of the paper containers. The sterilized paper container is filled with a content sterilized by an apparatus separately provided by a filling device 42. Further, the paper container is folded by a top part folding device along a line defining a top part thereof, the inner surface of the top part is heated by a top part heating device 43, and the heated part is crimped by a top part sealing device 44. In this way, the paper container is sealed. The sealed paper container is discharged from the chamber 33. As the paper container is conveyed in the chamber 33 of the aseptic filler shown in FIG. 4, the paper container is formed, and the formed paper container is sterilized, filled with a content, and sealed. The chamber 33 houses a paper container forming portion, a sterilizing portion, a filling portion and a sealing portion.

Before operation of the aseptic filler, the interior of the chamber 33 is subjected to the COP treatment and the SOP treatment. In this process, when removing the cleaning liquid used for the COP treatment or removing the aseptic water used for the SOP treatment, the transfer devices that convey the paper containers are driven to remove the cleaning liquid and the aseptic water deposited on the transfer devices. That is, the turret 34 with the mandrels 35 on which sleeves are yet to be fitted is rotated, and the conveyor 39 for transferring paper containers that is yet to hold paper containers is driven. By driving the turret 34 and the conveyor 39, the cleaning liquid or aseptic water deposited on the turret 34 and the conveyor 39 can be removed in a short time.

Figure 5:
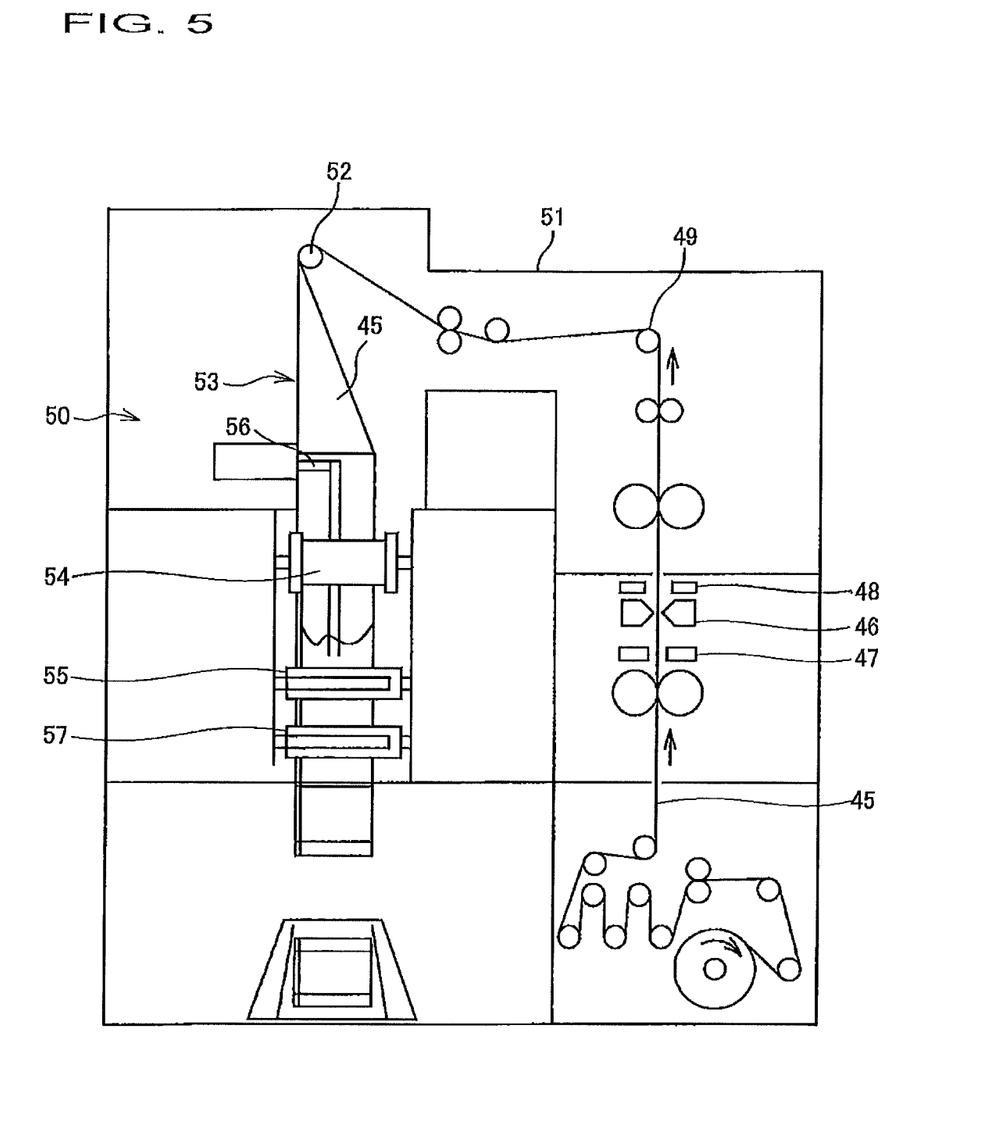
FIG. 5 is a schematic elevation view of an aseptic filler for pouches according to an embodiment of the present invention.

FIG. 5 is a schematic elevation view of an aseptic filler for pouches according to an embodiment of the present invention. The aseptic filler for pouches shown in FIG. 5 is an apparatus that is supplied with a film, sterilizes the supplied film, shapes the film into a pouch, fills the pouch with a sterilized content and seals the pouch. Therefore, the aseptic filler includes a feeder device for a packaging film 45, and a nozzle 46 that blasts a sterilizer to both surfaces of the packaging film 45. The feeding device for the packaging film 45 is a driving device for continuously feeding the packaging film 45 from a feed roll of the packaging film 45, and includes an infeed roller, various kinds of guide rollers arranged along the traveling path of the packaging film 45, and guide rollers that hold the packaging film 45 therebetween.

There are arranged guide rollers that guide the packaging film 45 fed from the feed roll to the sterilizer blasting nozzle 46, a preheating device 47 that heats the packaging film 45 before a sterilizer is blasted to the packaging film 45, and a heated air blasting apparatus 48 that blasts heated air to both surfaces of the packaging film 45 after the sterilizer is blasted to the packaging film 45.

The sterilized packaging film 45 is changed in direction by a roller 49 and conveyed to a filling and sealing portion 50. The filling and sealing portion 50 is shielded by a chamber 51, and the interior of the chamber 51 is subjected to the COP treatment and the SOP treatment before operation of the aseptic filler. The packaging film 45 conveyed into the filling and sealing portion 50 is changed in conveyance direction to the downward direction by a roller 52. After that, a former 53 folds over the opposite side edges of the packaging film 45 along the conveyance direction. The folded packaging film 45 passes between a pair of lengthwise sealing rollers 54 (FIG. 5 shows only the one on the near side). Meanwhile, the lengthwise sealing rollers 54 heat and weld the overlaid parts of the opposite side edges of the packaging film 45, thereby forming the packaging film 45 into a cylindrical shape. After that, a pair of crosswise sealing rollers 55 heat and weld the packaging film 45 at regular intervals in the conveyance direction, thereby sealing the packaging film 45 in the crosswise direction. The cylindrical packaging film 45 to be sealed crosswise is continuously supplied with various kinds of sterilized contents through a supply pipe 56, and the crosswise sealing is sealed with liquid sandwiched between that seals the packaging film 45 at parts in which there is the content. After that, a notch for each pouch is formed in the packaging film 45 as required, and perforations are formed for each pouch in the crosswise direction, or the packaging film 45 is cut into pouches at the crosswise sealed parts by a cutting roller 57. The resulting pouches fall into a discharging portion.

Before operation of the aseptic filler, the interior of the chamber 51 is subjected to the COP treatment and the SOP treatment. Before performing the SOP treatment, the packaging film 45 is introduced into the chamber 51. This is because the packaging film 51 cannot be introduced into the chamber 51 subjected to the SOP treatment without opening the chamber 51. In this process, when removing the cleaning water used for the COP treatment or removing the aseptic water used for the SOP treatment, the rollers for nipping and transferring a packaging film 45, the lengthwise sealing rollers 54, the crosswise sealing rollers 55 and the cutting roller 57, which are transfer devices for transferring the packaging film 45, are driven to remove the cleaning liquid and the aseptic water deposited on the transfer devices. That is, by driving the rollers, which are transfer devices for the film 45 to be shaped, while feeding the film to the rollers, the cleaning liquid or aseptic water deposited on the rollers, which are transfer devices, can be removed in a short time. The packaging film 45 is conveyed into the chamber 51 after a sterilizer is blasted to the packaging film 45 by a sterilizer blasting apparatus 46. In order to perform the SOP treatment of the interior of the chamber 51 with reliability, the packaging film 45 to be conveyed into the chamber 51 has to be sterilized before being conveyed into the chamber 51.

Although the present invention is configured as described above, the present invention is not limited to the embodiment described above, and various modifications are possible without departing from the scope and spirit of the present invention.

REFERENCE SIGNS LIST

1 chamber
2 rotary nozzle
3 twin-fluid nozzle
4 filling portion chamber
11 introduction wheel
12 filling wheel
14 capper wheel
15 discharging wheel

The invention claimed is:

1. A method for sterilizing an interior of an aseptic filler chamber before operation of the aseptic filler, the aseptic filler filling a sterilized container with a sterilized content in an aseptic atmosphere and sealing the container filled with the content,
   wherein after the interior of the chamber of the aseptic filler is cleaned by spraying a cleaning liquid into the chamber, a transfer device or transfer devices for transferring the container is or are driven intermittently to remove any of the cleaning liquid deposited on the transfer device, and a sterilizer is then sprayed into the chamber of the aseptic filler.

2. The method for sterilizing an interior of an aseptic filler chamber according to claim 1, wherein the sterilizer contains hydrogen peroxide.

3. The method for sterilizing an interior of an aseptic filler chamber according to claim 1, wherein the sterilizer contains peracetic acid.

4. The method for sterilizing an interior of an aseptic filler chamber according to claim 1, wherein the cleaning liquid is aseptic water.

5. The method for sterilizing an interior of an aseptic filler chamber according to claim 1, wherein when driving the transfer device, heated aseptic air is blown into the chamber of the aseptic filler.

6. The method for sterilizing an interior of an aseptic filler chamber according to claim 1, wherein transfer devices in a plurality of chambers of the aseptic filler are driven on a chamber basis.

7. The method for sterilizing an interior of an aseptic filler chamber according to claim 2, wherein the cleaning liquid is aseptic water.

8. The method for sterilizing an interior of an aseptic filler chamber according to claim 3, wherein the cleaning liquid is aseptic water.

9. The method for sterilizing an interior of an aseptic filler chamber according to claim 2, wherein when driving the transfer device, heated aseptic air is blown into the chamber of the aseptic filler.

10. The method for sterilizing an interior of an aseptic filler chamber according to claim 3, wherein when driving the transfer device, heated aseptic air is blown into the chamber of the aseptic filler.

11. The method for sterilizing an interior of an aseptic filler chamber according to claim 4, wherein when driving the transfer device, heated aseptic air is blown into the chamber of the aseptic filler.

12. The method for sterilizing an interior of an aseptic filler chamber according to claim 2, wherein transfer devices in a plurality of chambers of the aseptic filler are driven on a chamber basis.

13. The method for sterilizing an interior of an aseptic filler chamber according to claim 3, wherein transfer devices in a plurality of chambers of the aseptic filler are driven on a chamber basis.

14. The method for sterilizing an interior of an aseptic filler chamber according to claim 4, wherein transfer devices in a plurality of chambers of the aseptic filler are driven on a chamber basis.

15. The method for sterilizing an interior of an aseptic filler chamber according to claim 5, wherein transfer devices in a plurality of chambers of the aseptic filler are driven on a chamber basis.

* * * * *